United States Patent [19]
Luebke et al.

[11] Patent Number: 6,069,284
[45] Date of Patent: May 30, 2000

[54] PROCESS FOR SEPARATING DIISOPROPYL ETHER FROM ISOPROPYL ALCOHOL AND WATER

[75] Inventors: Charles P. Luebke, Mount Prospect; William A. Leet, Naperville, both of Ill.

[73] Assignee: UOP LLC, Des Plaines, Ill.

[21] Appl. No.: 09/099,042

[22] Filed: Jun. 17, 1998

[51] Int. Cl.[7] .................................................. C07C 41/00
[52] U.S. Cl. ........................ 568/697; 568/694; 568/699
[58] Field of Search .................................. 568/694, 697, 568/699

[56] References Cited

U.S. PATENT DOCUMENTS

| | | | |
|---|---|---|---|
| 4,182,914 | 1/1980 | Imaizumi | 568/697 |
| 4,857,664 | 8/1989 | Huang et al. | 568/697 |
| 4,906,787 | 3/1990 | Huang et al. | 568/697 |
| 5,057,629 | 10/1991 | Diaz et al. | 568/699 |
| 5,113,024 | 5/1992 | Harandi et al. | 568/697 |
| 5,154,801 | 10/1992 | Harandi et al. | 203/43 |
| 5,208,387 | 5/1993 | Harandi et al. | 568/695 |
| 5,324,866 | 6/1994 | Marker et al. | 568/697 |
| 5,371,301 | 12/1994 | Marker et al. | 568/694 |
| 5,504,257 | 4/1996 | Marker et al. | 568/694 |
| 5,600,023 | 2/1997 | Marker et al. | 568/694 |

*Primary Examiner*—James O. Wilson
*Attorney, Agent, or Firm*—John G. Tolomei; Frank S. Molinaro; Maryann Maas

[57] ABSTRACT

A process to separate diisopropyl ether from a mixture of diisopropyl ether, isopropyl alcohol, and water has been developed. The process begins with distilling, in a distillation column, the mixture into a bottoms stream containing water and isopropyl alcohol and an overhead stream containing an azeotrope of diisopropyl ether, isopropyl alcohol, and water. The overhead stream is condensed and allowed to form an aqueous phase enriched in isopropyl alcohol and water and an organic phase enriched in diisopropyl ether with some water and isopropyl alcohol in an overhead receiver. The aqueous phase is recycled to the distillation column. The organic phase is passed to a drier to form a bottoms product stream containing at least 99 mole percent diisopropyl ether and a drier overhead stream containing an azeotrope of diisopropyl ether, isopropyl alcohol, and water. The drier overhead stream is condensed and introduced to the overhead receiver described earlier to combine with the condensed overhead stream from the distillation column and to form the aqueous phase and an organic phase discussed above. The bottoms diisopropyl ether product stream from the drier is collected.

7 Claims, 1 Drawing Sheet

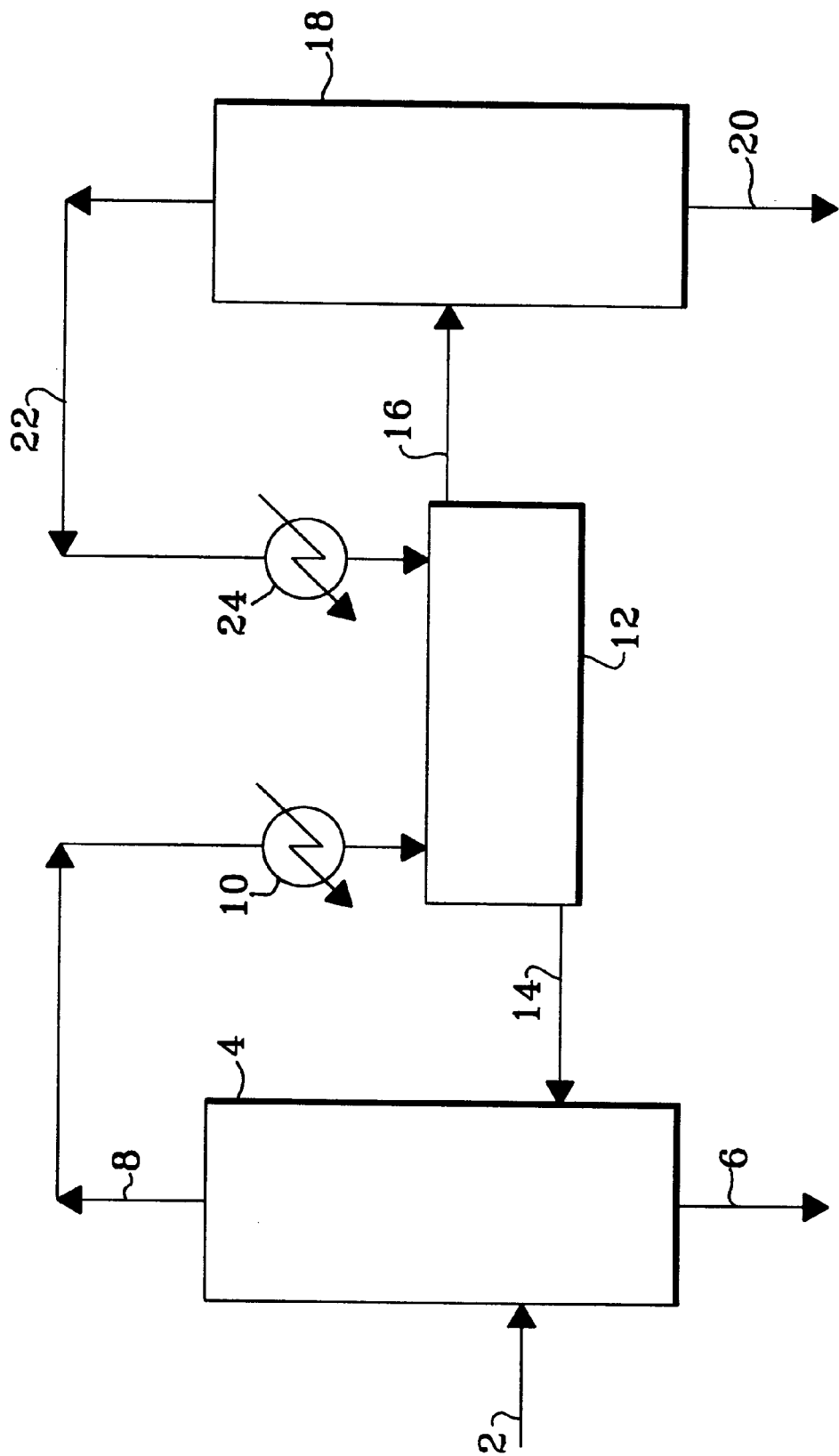

PROCESS FOR SEPARATING DIISOPROPYL ETHER FROM ISOPROPYL ALCOHOL AND WATER

BACKGROUND OF THE INVENTION

The separation of diisopropyl ether from isopropyl alcohol and water has been a challenging separation due to the azeotropes that form. U.S. Pat. No. 5,154,801 describes a separation process designed to specifically avoid forming an isopropyl alcohol-water azeotrope during the effluent processing of a diisopropyl ether production process. Most of the time azeotropes do form and, historically, approaches to perform the separation have included adsorption, U.S. Pat. No. 5,057,629, solvent Extraction, U.S. Pat. No. 4,182,914, and distillation followed by decantation, U.S. Pat. No. 4,857,664. By far the most popular approach has been water washing, see U.S. Pat. No. 4,906,787, U.S. Pat. No. 5,208,387, U.S. Pat. No. 5,113,024, U.S. Pat. No. 5,504,257, U.S. Pat. No. 5,324,866, U.S. Pat. No. 5,371,301 and U.S. Pat. No. 5,600,023. Water washing, although effective and successful, has several drawbacks. The first involves the high quantity of water that must be maintained within the system to perform the washing. A water wash unit and more conduits become necessary and the size of some vessels is increased to accommodate the high quantity of water, all of which increases the cost of the system. Another drawback arises when the spent water is recycled back to a distillation column to regenerate wash water. Utility costs increase under the burden of continually reboiling a large quantity of water.

The present invention provides an alternative that advantageously uses the diisopropyl ether-isopropyl alcohol-water azeotrope to separate diisopropyl ether from a mixture of diisopropyl ether, isopropyl alcohol and water. The azeotrope is intentionally formed and first used to draw substantially all of the diisopropyl ether present in a mixture into an overhead stream of a distillation column. The overhead stream is condensed and an aqueous phase and an organic phase are formed. The organic phase is passed to a drier column, while the aqueous phase is recycled to the distillation column. In the drier column, the diisopropyl ether-isopropyl alcohol-water azeotrope is again intentionally formed and now used to draw substantially all of the water and isopropyl alcohol into a drier overhead stream. Since isopropyl alcohol and water were removed in the aqueous phase of the previous column, it is now possible to form the desired bottoms diisopropyl ether product stream containing virtually no water or isopropyl alcohol. Using the present invention achieves the desired separation while also eliminating the need for a water wash unit and additional conduits, and lowering the utility cost by eliminating the need to reboil a large quantity of spent wash water.

SUMMARY OF THE INVENTION

The purpose of the invention is to separate diisopropyl ether from a mixture of diisopropyl ether, isopropyl alcohol, and water. The process begins with distilling, in a distillation column, the mixture into a bottoms stream containing water and isopropyl alcohol and an overhead stream which is an azeotrope of diisopropyl ether, isopropyl alcohol, and water. The bottoms stream is removed and the overhead stream is condensed and allowed to form an aqueous phase enriched in isopropyl alcohol and water and an organic phase enriched in diisopropyl ether with some water and isopropyl alcohol in an overhead receiver. The aqueous phase is recycled to the distillation column. The organic phase is passed to a drier column to form a bottoms product stream containing at least 99 mole percent diisopropyl ether and a drier overhead stream containing an azeotrope of diisopropyl ether, isopropyl alcohol, and water. The drier overhead stream is condensed and introduced to the overhead receiver described earlier where it is combined with the condensed overhead stream from the distillation column and allowed to form the aqueous phase and the organic phase discussed above. The bottoms diisopropyl ether product stream from the drier is collected.

BRIEF DESCRIPTION OF THE DRAWING

The figure is a schematic representation of the separation process of the present invention. The drawing has been simplified by the deletion of a large number of pieces of apparatus customarily employed in processes of this nature which are not specifically required to illustrate the performance of the invention.

DETAILED DESCRIPTION OF THE INVENTION

The present invention provides an efficient, reduced cost process for separating diisopropyl ether from a feed mixture of diisopropyl ether, isopropyl alcohol, and water. The feed mixture is typically the effluent of a diisopropyl ether production process. The mixture is introduced to a distillation column that is operating at a pressure ranging from about 34 kPag (5 psig) to about 1,724 kPag (250 psig). The temperatures within the distillation column are readily determined from the operating pressure selected. In this distillation column, a large portion of the higher boiling material, isopropyl alcohol and water are readily separated from the mixture. Most of the isopropyl alcohol and water flow to the bottom of the column and are removed in a bottoms stream. The isopropyl alcohol and water bottoms stream may be recycled to a reactor such as a diisopropyl ether formation reactor. However, not all of the isopropyl alcohol and water are removed from the distillation column in the bottoms stream. As isopropyl alcohol and water are removed from the feed mixture, an isopropyl alcohol-water-diisopropyl ether azeotrope will form. The exact concentrations of the components in the azeotrope will depend upon the pressure at which the column is operated. For example, at a pressure of 172 kPag (25 psig) the azeotrope will contain about 16.5 mole percent isopropyl alcohol, 16.1 mole percent water, and 67.4 mole percent diisopropyl ether. The azeotrope is readily separated from isopropyl alcohol and water due to the significant difference between the boiling points of the azeotrope and the alcohol-water mixture. The azeotrope is removed from the distillation column in an overhead stream, also termed herein as a first overhead stream. Enough isopropyl alcohol and water should be present in the distillation column so that substantially all of the diisopropyl ether is drawn into the azeotrope. "Substantially all" as used herein means greater than 99 mole percent. Very little if any of the diisopropyl ether is lost through the bottoms stream.

The overhead stream is condensed and allowed to separate in an overhead receiver. The overhead stream may be condensed using cooling water or by sub-cooling and generally the condensing is conducted at temperatures ranging from about 24° C. (75° F.) to about 93° C. (200° F.). The act of cooling the overhead stream separates the stream into two phases, an aqueous phase and an organic phase, and breaks the azeotrope mixture. The lower the temperature to which the overhead stream is cooled, the greater the degree of separation achievable in the overhead receiver. For example, sub-cooling the overhead stream may improve the phase separation between the organic phase and the aqueous phase. However, the preferred temperatures are those attainable with readily available cooling water. Usually refrigeration or other means of sub-cooling the overhead stream is costly, thereby making their use less preferred. In the overhead receiver, a large portion of the water and isopropyl alcohol is separated into the aqueous phase, and a large portion of the diisopropyl ether is separated into the organic phase. Neither phase is pure, however, and each phase will contain some portion of the three individual components. It is expected that the aqueous phase may contain from about 1 to about 5 mole percent diisopropyl ether, and the organic phase may contain from about 10 to about 30 mole percent isopropyl alcohol and from about 5 to about 20 mole percent water. The aqueous phase is removed from the overhead receiver and recycled to the distillation column. Recycling the water and isopropyl alcohol helps to ensure that the distillation column contains sufficient water and isopropyl alcohol to draw substantially all of the diisopropyl ether into the azeotropic overhead. The organic phase is withdrawn from the overhead receiver and passed to a drier column.

The drier column is a distillation column operated at pressures ranging from about 34 kPag (5 psig) to about 1,724 kPag (250 psig). The operating temperatures of the drier column are readily determined from the selected operating pressure. The object of the drier column is to provide high purity diisopropyl ether or, in other words, a diisopropyl ether product stream containing at least 99 mole percent diisopropyl ether. As the organic phase from the overhead receiver enters the drier column, diisopropyl ether begins to be separated from the mixture due to the significant difference in the boiling points of the components. The diisopropyl ether is removed from the drier column in a bottoms product stream which contains at least 99 mole percent diisopropyl ether and preferably at least 99.5 mole percent diisopropyl ether. When sufficient diisopropyl ether has been separated, an isopropyl alcohol-water-diisopropyl ether azeotrope will form. As before, the exact concentrations of the components in the azeotrope will depend upon the pressure at which the column is operated. For example, at a pressure of 172 kPag (25 psig) the azeotrope will contain 16.5 mole percent isopropyl alcohol, 16.1 mole percent water, and 67.4 mole percent diisopropyl ether. The azeotrope is readily separated from diisopropyl ether due to the significant difference between the boiling points of the azeotrope and the ether. Such an excess of diisopropyl ether is present in the drier column that substantially all of the water and isopropyl alcohol are drawn into the formation of the azeotrope, thereby leaving little isopropyl alcohol or water to contaminate the bottoms diisopropyl ether product stream. The azeotrope is removed from the drier column in an overhead stream, also termed herein as a second overhead stream.

The overhead stream from the drier is condensed and allowed to separate along with the condensed overhead stream from the distillation column in the overhead receiver discussed earlier. The overhead stream from the drier may be condensed using the same condenser as used for the overhead stream from the distillation column or using a second condenser. It is economically preferred to use a single condenser. Either way, both overhead streams are combined in the overhead receiver so that the aqueous phase from the combination of overhead streams is recycled to the distillation column and the organic phase from the combination of overhead streams is passed to the drier column.

Without intending any limitation on the scope of the present invention and as merely illustrative, this invention is explained below in specific terms as applied to the separation of diisopropyl ether from a diisopropyl ether formation process effluent containing a mixture of diisopropyl ether, isopropyl alcohol, and water. Referring to the figure, a feedstock containing 26.4 mole percent diisopropyl ether, 53.2 mole percent isopropyl alcohol and 20.4 mole percent water is conducted in line 2 to a distillation column 4. Distillation column 4 is operated at a pressure of 172 kPag (25 psig) and at temperatures of 96° C. (205° F.) at the top and 110° C. (230° F.) at the bottom. Due to the significant difference in boiling points, the isopropyl alcohol and water distill into the bottom portion of distillation column 4 and are removed in line 6. As isopropyl alcohol and water are removed, a diisopropyl ether-isopropyl alcohol-water azeotrope containing 16.5 mole percent isopropyl alcohol, 16.1 mole percent water and 67.4 mole percent diisopropyl ether is formed. The high volume of isopropyl alcohol and water present in distillation column 4 ensures that substantially all of the diisopropyl ether present is drawn into the azeotrope. The azeotrope is easily distilled from the excess isopropyl alcohol and water and removed in first overhead stream 8.

First overhead stream 8 is condensed using cooling water in condenser 10 and introduced into overhead receiver 12. In overhead receiver 12 the now liquid overhead stream separates into two phases, an organic phase and an aqueous phase. The organic phase contains 73 mole percent diisopropyl ether, 11 mole percent water, and 16 mole percent isopropyl alcohol and the aqueous phase contains 95 mole percent water, 5 mole percent isopropyl alcohol and trace amounts of diisopropyl ether. The aqueous phase is removed from overhead receiver 12 in line 14 and recycled to distillation column 4. The organic phase is removed from overhead receiver 12 in line 16 and introduced to drier column 18. Drier column 18 is a distillation column operated at a pressure of 172 kPag (25 psig) and at temperatures of 96° C. (205° F.) at the top and 110° C. (230° F.) at the bottom. In drier column 18 diisopropyl ether distills into the lower portion of the column and is removed in line 20 as a bottoms product stream. As diisopropyl ether is removed from the mixture, a diisopropyl ether-isopropyl alcohol-water azeotrope containing 16.5 mole percent isopropyl alcohol, 16.1 mole percent water, and 67.4 mole percent diisopropyl ether is formed. The high volume of diisopropyl ether present in distillation column 4 ensures that substantially all of the water and isopropyl alcohol present are drawn into the azeotrope. Very little, if any, water and isopropyl alcohol are left to contaminate diisopropyl ether product stream 20. Therefore, diisopropyl ether product stream 20 is of high purity, containing at least 99 mole percent diisopropyl ether. The azeotrope is removed from drier column 18 in a second overhead stream 22. Second overhead stream 22 is condensed in condenser 24 using cooling water and conducted to overhead receiver 12. In overhead receiver 12, the now liquid second overhead stream combines with the liquid first overhead stream from distillation column 4 and separates into an aqueous phase and an organic phase as discussed above. The process continues in this manner, and through the intentional formation of a diisopropyl ether-isopropyl alcohol-water azeotrope in the first distillation column, substantially all of the diisopropyl ether is carried over to the overhead receiver, and then through the intentional formation of the diisopropyl ether-isopropyl alcohol-water azeotrope in the drier column, substantially all of the isopropyl alcohol and water are removed in the overhead stream from the drier, thereby leaving little or no water and isopropyl alcohol to contaminate the diisopropyl ether product stream. The result is a high purity diisopropyl ether product stream.

It must be emphasized that the above description is merely illustrative of a preferred embodiment and is not intended as an undue limitation on the generally broad scope of the invention. Moreover, while the description is narrow in scope, one skilled in the art would understand how to extrapolate to the broader scope of the invention. For example, the operation where a single condenser is used to condense the overhead streams from both the distillation column and the drier column or where different operating conditions are used can be readily extrapolated from the foregoing description.

What is claimed is:

1. A process for separating diisopropyl ether from a mixture of diisopropyl ether, isopropyl alcohol, and water comprising:

a) distilling the mixture into a bottoms stream containing water and isopropyl alcohol and a first overhead stream which is an azeotrope of diisopropyl ether, isopropyl alcohol, and water;

b) removing the bottoms stream containing water and isopropyl alcohol;

c) condensing the first overhead stream to form an aqueous phase enriched in isopropyl alcohol and water and an organic phase enriched in diisopropyl ether;

d) recycling the aqueous phase to step (a);

e) distilling the organic phase to form a bottoms product stream containing at least 99 mole percent diisopropyl ether, and a second overhead stream which is an azeotrope of diisopropyl ether, isopropyl alcohol, and water;

f) recycling the second overhead stream to step (c);

g) collecting the bottoms product stream.

2. The process of claim 1 wherein the distillation of step (a) is conducted at pressures ranging from about 34 kPag or 5 psig to about 1,724 kPag or 250 psig.

3. The process of claim 1 wherein the distillation of step (e) is conducted at pressures ranging from about 34 kPag or 5 psig to about 1,724 kPag or 250 psig.

4. The process of claim 1 wherein the condensing of step (c) is conducted at temperatures ranging from about 24° C. or 75° F. to about 93° C. or 200° F.

5. The process of claim 1 wherein a single condenser is used to perform the condensing of step (c).

6. The process of claim 1 wherein at least two condensers are used to perform the condensing of step (c).

7. The process of claim 1 wherein the bottoms product stream contains at least 99.5 mole percent diisopropyl ether.

* * * * *